United States Patent [19]
Behr et al.

[11] Patent Number: 6,023,002
[45] Date of Patent: Feb. 8, 2000

[54] PROCESS FOR PREPARING HYDROFLUOROETHERS

[75] Inventors: Frederick E. Behr; Yuri Cheburkov, both of Woodbury, Minn.

[73] Assignee: 3M Innovative Properties Company, St. Paul, Minn.

[21] Appl. No.: 09/012,959

[22] Filed: Jan. 26, 1998

[51] Int. Cl.$^7$ .......................... C07C 41/05; C07C 41/22; C07C 51/60
[52] U.S. Cl. .................. 568/685; 568/683; 568/692; 568/697; 562/849; 562/851; 562/852
[58] Field of Search ................. 568/683, 685, 568/692, 697; 562/588, 849, 851, 852, 865

[56] References Cited

U.S. PATENT DOCUMENTS

| | | | |
|---|---|---|---|
| 3,900,372 | 8/1975 | Childs et al. | 204/81 |
| 5,466,877 | 11/1995 | Moore | 562/852 |
| 5,573,654 | 11/1996 | Cheburkov et al. | 205/430 |
| 5,637,772 | 6/1997 | Malik et al. | 564/505 |
| 5,741,950 | 4/1998 | Costello | 568/683 |

FOREIGN PATENT DOCUMENTS

| | | | |
|---|---|---|---|
| 61-69745 | 4/1986 | Japan | C07C 69/63 |
| 61-225150 | 10/1986 | Japan | C07C 53/50 |
| 63-035534 | 2/1988 | Japan | C07C 43/17 |
| WO 97/38962 | 10/1997 | WIPO | C07C 43/12 |

OTHER PUBLICATIONS

Hudlicky, Chemistry of Organic Fluorine Compounds, pp. 62, 285–289, 360–361, 380, 389, 392, 409, 496–500, 505, 617, and 654–657 ($2^{nd}$ ed. 1992).

Koshar et al., "The Addition of Alcohols to Octafluoroisobutene," J. Am. Chem. Soc., vol. 79, pp. 1741–1744 (1957).

Knunyants et al., "Alkylation of Hexametapol," Institute of Heteroorganic Compounds, Academy of Sciences of the USSR, p. 1279 (1971).

Knunyants et al., "Mosemeric Carbanions of Fluorine–Containing Monocarbonyls," Zhurnal Vses. Khim. Ob–va Im. Mendeleeva, vol. 15, pp. 17–30 (1970).

Knunyants et al., "Reactions of Fluoro Olefins," Institute of Heterooganic Compounds of the Academy of Sciences of the USSR, pp. 1387–1394 (1956).

Misaki, "Conversion of Methoxyperfluoroisobutene to α–Methylhexafluoroisobutyric acid Fluoride by a Phase Transfer Catalyst," Journal of Fluorine Chemistry, vol. 29, pp. 471–474 (1985).

Kocharyan et al., "Alkylating Properties of Alkyl Perfluoroisobutenyl Ethers," Institute of Heteroorganic Compounds, Academy of Sciences of the USSR, pp. 810–816 (1967).

Urushadze et al., "Alkylating Properties of Alkyl Fluoroalkenyl Ethers", Institute of Heteroorganic Compounds, Academy of Sciences of the USSR, pp. 1298–1303 (1970).

Snegirev et al., "Alkylating Properties of Fluorine–Containing Vinylic Ethers," Journal of Fluorine Chemistry, vol. 17, pp. 441–445 (1981).

Knunyants et al., "Alkylating Properties of Alkyl Perfluoroisobutenyl Ethers," Institute of Heteroorganic Compounds, Academy of Sciences of the USSR, pp. 93–98 (1969).

Knunyants et al., "Reaction of Alkyl Perfluoroisobutenyl Ethers with Triethyl Phosphite," Institute of Heteroorganic Compounds, Academy of Sciences of the USSR, p. 1281 (1971).

Cheburkov et al., "α–Hydrohexafluoroisobutyryl Fluoride—A New System with a Labile Hydrogen Atom," Institute of Heteroorganic Compounds, Academy of Sciences of the USSR, pp. 339–341 (1963).

Knunyants et al., "Bistrifluoromethylketene," Institute of Heteroorganic Compounds, Academy of Sciences of the USSR, pp. 985–991 (1965).

*Primary Examiner*—Ralph Gitomer
*Assistant Examiner*—Marjorie A. Moran
*Attorney, Agent, or Firm*—Kent S. Kokko

[57] ABSTRACT

Described is a reaction of a fluorinated alkoxide with an alkyl fluorovinylalkyl ether, the alkyl fluorovinylalkyl ether having alpha-beta carbon-carbon unsaturation relative to the ether oxygen, to produce a hydrofluoroether.

24 Claims, No Drawings

PROCESS FOR PREPARING HYDROFLUOROETHERS

FIELD OF THE INVENTION

The invention relates to reaction of a fluorinated alkoxide with an alkyl fluorovinylalkyl ether to prepare a hydrofluoroether.

BACKGROUND

Hydrofluoroethers (HFEs) are a class of commercially valuable chemical compounds. In a number of applications hydrofluoroethers have been found to be useful replacements for chlorofluorocarbons (CFCs), the use of which is presently disfavored and regulated due to the adverse effects CFCs are believed to have on the environment. Hydrofluoroethers have been found to be less harmful to the earth's ozone layer than CFCs because, for one thing, they are typically more easily degraded within the earth's atmosphere (they exhibit a low "ozone depletion potential").

Hydrofluoroethers have been found to be useful in a number of important industrial and commercial applications. They can be used alone or in combination with other chemicals, e.g., in applications where CFCs have been used in the past (as a solvent, a cleaning fluid, a polymerization medium, a fire extinguishing medium, a heat transfer agent, a refrigerant, or as a metal working agent in the cutting or forming of metals). With increasing demand for hydrofluoroethers, there exists an ongoing need to identify efficient methods for their production.

Hydrofluorocarbons (HFCs), which include a very wide variety of organic compounds composed of hydrogen, fluorine, and carbon, are also important industrial and commercial chemicals for use in applications such as in firefighting compositions, gaseous dielectrics, sterilant carriers, refrigerants, heat transfer fluids, cleaning fluids, and solvent applications, etc. As a single example, HFC-236 ($C_3F_6H_2$) is useful as a refrigerant as a replacement for CFC- 11, CFC-113 and CFC-114. There is continuing need for efficient methods of preparing a variety of different commercially useful HFCs such as HFC-236.

SUMMARY OF THE INVENTION

The present invention provides a method of reacting a fluorinated alkoxide with an alkyl fluorovinylalkyl ether. According to the invention, a fluorinated alkoxide can be reacted with a fluorinated vinyl ether to produce a hydrofluoroether. At the same time can be produced a conjugate base of a fluorinated carbonyl compound which may be further processed to produce other useful chemical compounds (e.g., hydrofluorocarbons). Thus, the inventive method provides not only a method of producing valuable and useful hydrofluoroethers, but at the same time can provide fluorinated carbonyl compounds that can be further reacted to produce other useful chemical compounds such as hydrofluorocarbons. The invention allows two classes of useful compounds to be produced, achieving efficiencies that could not be met by methods in the prior art.

An aspect of the invention relates to the reaction of a fluorinated alkoxide with an alkyl fluorovinylalkyl ether having alpha-beta carbon-carbon unsaturation relative to the ether oxygen, to produce a hydrofluoroether. The resultant hydrofluoroether can be of any chemical identity, and will depend upon the chosen reactants.

Another aspect of the invention relates to a process for preparing a hydrofluoroether. The process includes the steps of providing an alkyl fluorovinylalkyl ether; providing a fluorinated alkoxide; and reacting the alkyl fluorovinylalkyl ether with the fluorinated alkoxide to produce a hydrofluoroether.

A specific embodiment of the invention relates to a process for preparing a hydrofluoroether and a hydrofluorocarbon. The process includes the steps of providing an alkyl fluorovinylalkyl ether; providing a fluorinated alkoxide; reacting the alkyl fluorovinylalkyl ether with the fluorinated alkoxide to produce a hydrofluoroether and a conjugate base of a fluorinated carbonyl compound; treating the conjugate base of the fluorinated carbonyl compound with water to produce an alpha-hydro carbonyl compound; and, if the alpha-hydro carbonyl compound comprises a carboxylic acid, decarboxylating the alpha-hydro carbonyl compound to form a hydrofluorocarbon.

Within the present description, the following terms will be given the designated meanings:

"Fluorinated," as in fluorinated aliphatic, and the prefix "fluoro-," as in fluorovinylalkyl, refer to organic chemical moieties in which at least one carbon-bonded hydrogen atom has been replaced by fluorine.

"perfluorinated" and the prefix "perfluoroalkyl-" refer to organic chemical moieties in which essentially all carbon-bonded hydrogen atoms in an alkyl group have been replaced by fluorine atoms, e.g., at least 95 percent, preferably at least 99 percent, of all hydrogen atoms have been replaced with fluorine.

"hydrofluorocarbon" refers to compounds composed of carbon, hydrogen and fluorine atoms.

"hydrofluoroether" and "HFE" refer to fluoroalkyl-alkyl ether compounds.

DETAILED DESCRIPTION

According to the invention, an alkyl fluorovinylalkyl ether can be reacted with a fluorinated alkoxide to produce a hydrofluoroether.

The alkyl fluorovinylalkyl ether can be any ether compound comprising an ether-bonded alkyl component (R) and an ether-bonded fluorovinylalkyl component, where the ether-bonded fluorovinylalkyl component includes carbon-carbon unsaturation between the alpha and beta carbons (alpha-beta unsaturation) relative to the ether oxygen. Examples of such alkyl fluorovinylalkyl ether compounds include those of general formula I:

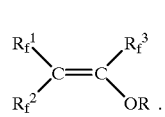

(I)

In formula I, $R_f^1$, $R_f^2$ and $R_f^3$ are independently fluorine atoms or fluorinated aliphatic groups preferably having from 1 to 10 carbon atoms which may be linear, branched, or cyclic, and which may optionally contain a catenary ether oxygen atom, or be unsaturated. R can be any alkyl that is sufficiently sterically unhindered to allow reaction with a fluorinated alkoxide. Preferably $R_f^1$, $R_f^2$, and $R_f^3$ are each, independently, F or a perfluorinated aliphatic group having from 1 to 10 carbon atoms, and which may be linear, branched, or cyclic, and which may optionally contain a catenary ether oxygen atom. R is preferably a linear or branched alkyl having from 1 to 6 carbon atoms, and preferably having a non-tertiary carbon atom bonded directly to the ether oxygen. Also optionally, the alkyl fluorovinylalkyl ether can be di-functional with respect to the vinyl moiety, i.e., a bis-vinyl ether; in such instance a resulting carbonyl compound reaction product (see below) can be a bis-carbonyl compound.

Alkyl fluorovinylalkyl ethers can be prepared by known methods. One such method is the addition of an alcohol to a fluoroalkene, followed by dehydrofluorination of the intermediate addition product. See M. Hudlicky, Chemistry of Organic Fluorine Compounds, pp. 285–9 and 409 ($2^{nd}$ ed. 1992). Preferred alkyl fluorovinylalkyl ethers can be derived from PFIB (octafluoroisobutylene) and lower alcohols (e.g., ethanol or methanol) as described by Koshar et al., J.Am. Chem. Soc., 79, 1741 (1957).

Some examples of useful alkyl fluorovinylalkyl ethers include the following:

$CF_2$=$CFOR$ $CF_3CF$=$CFOR$ $(CF_3)_2C$=$CFOR$ $(CF_3)_2C$=$C(C_2F_5)OR$ $(CF_3)_2C(OR)C[CF(CF_3)_2]$=$C(OR)CF_3$ $CF_3C(OR)$=$C[CF(CF_3)_2]_2$ $CF_2$=$C(CF_3)C(CF_3)$=$CFOR$ $C_2F_5CF(CF_3)C(C_2F_5)$=$CFOR$ $C_2F_5CF(CF_3)C(CF_3)$=$C(CF_3)OR$ $CF_3(OR)C$=$C(CF_3)C(CF_3)$=$C(OR)CF_3$

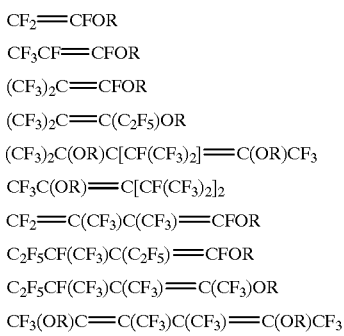

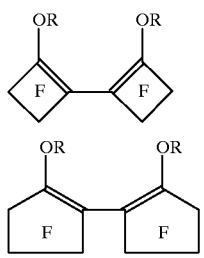

wherein each R is independently an alkyl group preferably having from about 1 to 10, more preferably from about 1 to 6 carbons.

The fluorinated alkoxide can be any fluorinated alkoxide capable of reacting with the alkyl fluorovinylalkyl ether. An example of useful fluorinated alkoxides include those of general formula II:

$$R_f\text{—}O^-M^+ \quad (II)$$

In formula II, $M^+$ describes a cation such as $Na^+$, $K^+$, $Li^+$, $NR_4^+$ (wherein R comprises, e.g., a lower alkyl), etc., and $R_f$ can be a linear or branched fluoroaliphatic group preferably having from 1 to 10 carbon atoms, optionally containing a catenary ether oxygen of trivalent nitrogen, and preferably being perfluorinated.

The fluorinated alkoxide can be derived from a fluorinated alkoxide precursor, (also referred to herein as "the precursor") as is well known in the chemical art, and according to a number of different, known methods. A number of exemplary fluorinated alkoxide precursors and corresponding fluorinated alkoxides are shown below:

| Precursor | Fluorinated Alkoxide |
|---|---|
| $CF_2(O)$ | $CF_3O^-M^+$ |
| $CF_3C(O)F$ | $C_2F_5O^-M^+$ |
| $C_2F_5C(O)F$ | $C_3F_7O^-M^+$ |
| $C_3F_7C(O)F$ | $C_4F_9O^-M^+$ |
| $C_4F_9C(O)F$ | $C_5F_{11}O^-M^+$, |
| $C_5F_{11}C(O)F$ | $C_6F_{13}O^-M^+$ |
| $CF_3OCF_2C(O)F$ | $CF_3OC_2F_4O^-M^+$ |
| $(CF_3)_2C(O)$ | $(CF_3)_2CFO^-M^+$ |
| $(CF_3)_2NCF_2C(O)F$ | $(CF_3)_2NCF_2CF_2O^-M^+$ |
| $FC(O)CF_2C(O)F$ | $M^+\text{-}OC_3F_6O^-M^+$ |

According to one method of preparing a fluorinated alkoxide from a precursor, any of a fluorinated acyl fluoride, fluorinated acyl chloride, fluoroalkyl ester, a fluorinated anhydride, or a fluoroalkyl carbonate can be used as a suitable fluorinated alkoxide precursor (if a fluoroalkyl ester is used as a fluorinated alkoxide precursor, the carbon atom alpha to the ester oxygen should generally be at least di-fluorinated). These precursors can be converted to fluorinated alkoxides by contacting them with fluoride ion, e.g., in the form of an anhydrous alkali metal fluoride salt, in an anhydrous, polar, aprotic solvent, to generate a fluorinated alkoxide Rf—O⁻ (the fluorinated alkoxide typically exists in solution in an ionic form, $R_f$—O⁻). The fluoride ion can generally be reacted with the precursor in a stoichiometric amount, or perhaps a slight excess; a large excess of fluoride ion is undesirable due to the possibility that it be present to react with the alkyl fluorovinylalkyl ether.

As a single example, a fluorinated acyl fluoride can be reacted with potassium fluoride to produce a corresponding fluorinated alkoxide, as follows:

$R_f'$ can be a linear or branched fluoroaliphatic group. $R_f'$ preferably has from 1 to 6 carbon atoms. In the above reaction scheme, $R_f'$ $CF_2$— in the fluorinated alkoxide corresponds to the group defined in formula II as $R_f$.

Examples of compounds that can be useful as fluorinated alkoxide precursors include fluorinated acyl fluorides, fluorinated acyl chlorides, fluoroalkyl esters, fluorinated anhydrides, and fluoroalkyl carbonates, and are exemplified as follows: $CF_3C(O)F$, $C_2F_5C(O)F$, $C_3F_7C(O)F$, $C_4F_9C(O)F$, $C_5F_{11}C(O)F$, $CF_3C(O)Cl$, $C_2F_5C(O)Cl$, $C_3F_7C(O)Cl$, $C_4F_9C(O)Cl$, $C_5F_{11}C(O)Cl$, $CF_3CO_2CF_3$, $C_2F_5CO_2C_2F_5$, $C_3F_7CO_2C_3F_7$, $C_4F_9CO_2C_4F_9$, $C_5F_{11}CO_2C_5F_{11}$, $CF_3C(O)$—$O$—$C(O)CF_3$, $C_2F_5C(O)$—$O$—$C(O)C_2F_5$, $C_3F_7C(O)$—$O$—$C(O)C_3F_7$, $C_4F_9C(O)$—$O$—$C(O)C_4F_9$, $C_5F_{11}C(O)$—$O$—$C(O)C_5F_{11}$, $CF_3OC(O)OCF_3$, $CF_3CF_2OC(O)OCF_2CF_3$, $C_3F_7OC(O)OC_3F_7$, etc.,

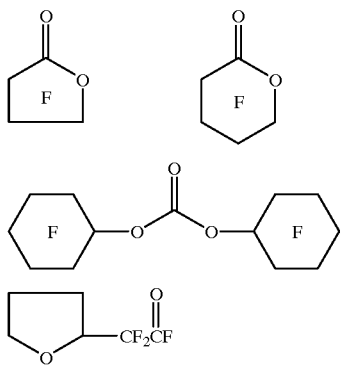

as well as partially fluorinated analogues thereof.

In a second method of producing a useful fluorinated alkoxide, a fluorinated alkoxide can be derived from a fluoroketone. A fluoroketone can be converted to a fluorinated alkoxide by reaction with a stoichiometric amount (or a slight excess, as described above) of anhydrous alkali metal fluoride to generate a secondary fluoroalkoxide.

Each $R_f'$ can independently be as defined above. It can be preferred that in the ketone precursor, at least one of the $R_f'$ groups have a primary carbon atom alpha to the carbonyl. Most preferably with respect to ketone fluorinated alkoxide precursors, one of the $R_f'$ groups is —$CF_3$. With respect to the above reaction scheme, $R_f'R_f'$ CF— corresponds to the group defined in formula II as $R_f$.

Fluoroketones can be prepared, e.g., by methods described in M. Hudlicky, Chemistry of Organic Fluorine Compounds, pp. 62, 360–1, 380, 389, 392, 505, 617, and 654–7 ($2^{nd}$ed. 1992).

Examples of fluoroketones useful as fluorinated alkoxide precursors include, for example: $CF_3C(O)CF_3$, $C_2F_5C(O)C_2F_5$, $C_3F_7C(O)C_3F_7$, $C_4F_9C(O)C_4F_9$, $C_4F_9C(O)CF_3$, $HC_4F_8C(O)CF_3$,

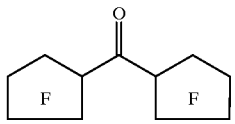

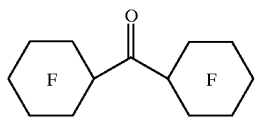

A fluorinated alkoxide can also be prepared by reacting a fluorinated tertiary alcohol fluorinated alkoxide precursor with a stoichiometric amount (or slight excess) of base, e.g., potassium hydroxide or sodium hydride, in a polar, aprotic solvent, to produce a tertiary fluorinated alkoxide:

Each $R_f'$ can independently be a linear or branched fluoroaliphatic group, preferably having from about 1 to 6 carbon atoms. In this reaction scheme $R_f'R_f'R_f'$ C— corresponds to the group defined in formula II as $R_f$.

Examples of suitable tertiary alcohols for use as precursors to a fluorinated alkoxide include $(CF_3)_3COH$, $(CF_3)_2C(C_2F_5)OH$, and $(CF_3)_2CFCF_2C(CF_3)_2OH$.

Fluorinated acyl fluorides are well known in the chemical art, and can be prepared by electrochemical fluorination (ECF) of a corresponding hydrocarbon carboxylic acid (or a derivative thereof), using either anhydrous hydrogen fluoride (Simons ECF) or KF.2HF (Phillips ECF) as the electrolyte. Fluoroalkyl esters and fluoroalkyl carbonates are also well known in the chemical art, and can be prepared from fluorinated acyl fluorides, or can be directly prepared by known methods such as fluorination of an appropriate organic precursor.

Fluorinated acyl fluorides and fluorinated ketones can also be prepared by dissociation of fluorinated carboxylic acid esters, which can be prepared from a hydrocarbon or partially-fluorinated carboxylic acid ester by direct fluorination with fluorine gas. Dissociation can be achieved by contacting the fluorinated carboxylic acid ester with a source of fluoride ion (see, e.g., U.S. Pat. No. 3,900,372 (Childs), the description of which is incorporated herein by reference) or by combining the ester with an initiating reagent such as a gaseous non-hydroxylic nucleophile, a liquid non-hydroxylic nucleophile, or a mixture of at least one non-hydroxylic nucleophile (gaseous, liquid, or solid) and at least one solvent which is inert to acylating agents. See also U.S. Pat. No. 5,466,877 (Moore), the description of which is incorporated herein by reference.

Suitable anhydrous polar aprotic solvents for use in the above reactions include acyclic ethers such as diethyl ether, ethylene glycol dimethyl ether, and diethylene glycol dimethyl ether; carboxylic acid esters such as methyl formate, ethyl formate, methyl acetate, diethyl carbonate, and propylene carbonate; alkyl nitriles such as acetonitrile; alkyl amides such as N,N-diethylformamide, and N-methylpyrrolidone; alkyl sulfoxides such as dimethyl sulfoxide; alkyl sulfones such as dimethylsulfone, tetramethylene sulfone, and other sulfolanes; oxazolidones such as N-methyl-2-oxazolidone; and mixtures thereof.

An example of the inventive reaction can be represented as follows:

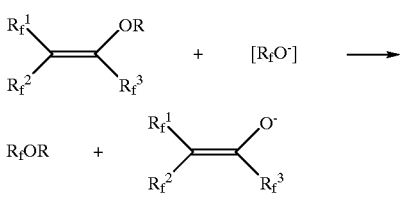

wherein an alkyl fluoroalkylvinyl ether is reacted with a fluorinated alkoxide to produce a hydrofluoroether and a conjugate base of a fluorinated carbonyl compound. In the above reaction scheme each of $R_f$, $R_f^1$, $R_f^2$, $R_f^3$, and R are as defined.

The reaction may be accomplished by preparing a reaction solution comprising the alkyl fluorovinylalkyl ether and the fluorinated alkoxide. The reaction can be carried out in any suitable reaction vessel, at ambient (e.g., atmospheric) pressure, although when volatile reactants are used or when volatile products are produced a pressure vessel can be preferred.

The amounts of the alkyl fluorovinylalkyl ether and fluorinated alkoxide reactants can be chosen as desired, but generally, for monovalent ether reactants the relative molar amounts of each reactant can be within a range from about a 1:1 molar ratio of alkyl fluorovinylalkyl ether to fluorinated alkoxide, to a 1:2 ratio. Similarly, for bis-alkyl fluorovinylalkyl ether reactants the molar ratio can preferably be in the range from about 1:1 to 1:4, bis-alkyl fluorovinylalkyl ether to fluorinated alkoxide.

Generally, heating of the reaction solution is not necessary, and the reaction can proceed at ambient temperature. Still, any temperature between 0° C. and 100° C. may be used, with ambient temperature being preferred. Mild heating e.g., to about 60° C., can be useful to cause production of a fluorinated alkoxide from its precursor, or to increase reaction rate of the alkyl fluorovinylalkyl ether and the fluorinated alkoxide. The course of the reaction can be monitored using standard analytical techniques, e.g., gas chromatography, to observe conversion of the reactants and product formation.

In a preferred method of the process of the invention, the fluorinated alkoxide can be initially generated in situ, i.e., within the reaction solution, for example, by adding a source of anhydrous fluoride ion, or a base, as appropriate, to a fluorinated alkoxide precursor dissolved in solvent (with mild heating if desired). Thereafter, the alkyl fluorovinylalkyl ether can be added to the reaction solution. The reactants may be charged at a temperature at or below room temperature (25 C.), and then warmed slightly to effect formation of the fluorinated alkoxide. The reaction solution may then be cooled to allow addition of the alkyl fluorovinylalkyl ether to the reactor.

A reaction product can include a hydrofluoroether having the structure $R_f$—O—R, wherein $R_f$ and R are as defined. Examples of a number of hydrofluoroethers are described, for example, in Assignee's copending U.S. patent application Ser. No. 08/649,361, having Attorney's Docket Number 51258USA4C, and filed May 17, 1996, now U.S. Pat. No. 5,962,390, issued Oct. 10, 1999. A number of specific, non-limiting examples of HFEs that can be prepared by the reaction include $C_3F_7OCH_3$, $C_3F_7OC_2H_5$, $C_3F_7OC_3H_7$, $C_3F_7OC_4H_9$, $C_3F_7OC_5H_{11}$, $C_3F_7OC_6H_{13}$, $C_4F_9OCH_3$, $C_4F_9OC_2H_5$, $C_4F_9OC_3H_7$, $C_4F_9OC_4H_9$, $C_4F_9OC_5H_{11}$, $C_4F_9OC_6H_{13}$, $C_5F_{11}OCH_3$, $C_5F_{11}OC_2H_5$, $C_5F_{11}OC_3H_7$, $C_5F_{11}OC_4H_9$, $C_5F_{11}OC_5H_{11}$, $C_5F_{11}OC_6H_{13}$, $C_6F_{13}OCH_3$, $C_6F_{13}OC_2H_5$, $C_6F_{13}OC_3H_7$, $C_6F_{13}OC_4H_9$, $C_6F_{13}OC_5H_{11}$, $C_6F_{13}OC_6H_{13}$, $C_7F_{15}OCH_3$, $C_7F_{15}OC_2H_5$, $C_7F_{15}OC_3H_7$, $C_7F_{15}OC_4H_9$, $C_7F_{15}OC_5H_{11}$, $C_7F_{15}OC_6H_{13}$, $C_8F_{17}OCH_3$, $C_8F_{17}OC_2H_5$, $C_8F_{17}OC_3H_7$, $C_8F_{17}OC_4H_9$, $C_8F_{17}OC_5H_{11}$, $C_8F_{17}OC_6H_{13}$, $CF_3OC_3F_6OCH_3$, $C_2F_5OC_2F_4OC_2H_5$, $CH_3OC_4F_8OCH_3$

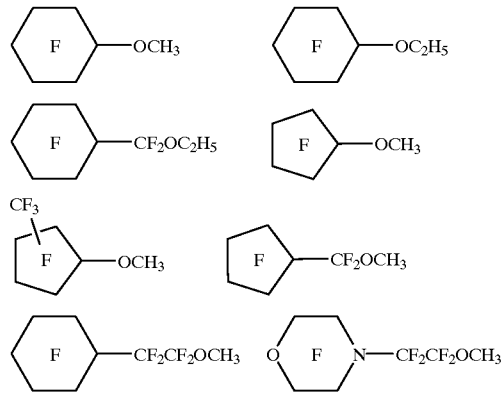

Another reaction product can be a conjugate base of a fluorinated carbonyl compound having the mesomeric carbanion structure:

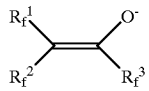

(This structure is shown without the presence of a stabilizing counterion, e.g., $M^+$ as previously defined). In the above formula, the identities of the $R_f^1$, $R_f^2$, and $R_f^3$ groups depend on the chemical identity of the alkyl fluorovinylalkyl ether reactant.

The immediate hydrofluoroether and conjugate base reaction products can be separated, and each can be individually processed or further reacted, as desired. Because the conjugate base reaction product exists as a non-volatile salt, while the hydrofluoroether is typically relatively more volatile, separation and isolation of the hydrofluoroether from the reaction solution can generally be accomplished by simple distillation or nitrogen purge methods.

Once the hydrofluoroether has been separated from the reaction solution, the conjugate base of the fluorinated carbonyl compound can be further processed or reacted to produce other useful and desired chemical compounds. For example, the conjugate base can be treated with water to produce an alpha-hydro carbonyl compound. If $R_f^3$ is a fluoroalkyl, the conjugate base of the fluorinated carbonyl compound reaction product will be a conjugate base of a fluoroketone. Upon treatment with water such a compound can yield an alpha-hydro fluoroketone.

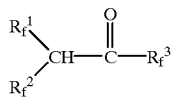

Exemplary alpha-hydro fluoroketones are shown in the table below with their corresponding alkyl fluorovinylalkyl ether reactants.

| alkyl fluorovinylalkyl ether reactant | fluorinated carbonyl compound |
|---|---|
| $(CF_3)_2C=C(C_2F_5)OR$ | $(CF_3)_2CHC(O)C_2F_5$ |
| $(CF_3)_2C(OR)C[CF(CF_3)_2]=C(OR)CF_3$ | $(CF_3)_2C(OR)CH[(CF(CF_3)_2]C(O)CF_3$ |
| $CF_3C(OR)=C[CF(CF_3)_2]_2$ | $CF_3C(O)CH[CF(CF_3)_2]_2$ |
| $CF_2=C(CF_3)C(CF_3)=CFOR$ | $CF_2=C(CF_3)CH(CF_3)C(O)F$ |
| $C_2F_5CF(CF_3)C(C_2F_5)=CFOR$ | $C_2F_5CF(CF_3)CH(C_2F_5)C(O)F$ |
| $C_2F_5CF(CF_3)C(CF_3)=C(CF_3)OR$ | $C_2F_5CF(CF_3)CH(CF_3)C(O)CF_3$ |
| $CF_3C(OR)=C(CF_3)C(CF_3)=C(OR)CF_3$ | $CF_3C(O)CH(CF_3)CH(CF_3)C(O)CF_3$ |

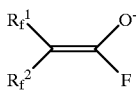

If $R_f^3$ is a fluorine atom, the conjugate base of the fluorinated carbonyl compound will be a conjugate base of a fluoroalkyl acyl fluoride having the mesomeric structure:

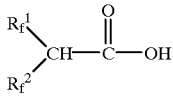

which, upon treatment with water, can yield an alpha-hydro fluoroalkyl carboxylic acid having the structure

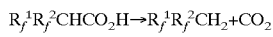

Exemplary alpha-hydro fluoroalkyl carboxylic acids and their corresponding alkyl fluorovinylalkyl ether reactants are shown in the table below.

| alkyl fluorovinylalkyl ether | fluorinated carbonyl compound |
|---|---|
| $CF_2=CFOR$ | $CHF_2CO_2H$ |
| $CFCl=CFOR$ | $CHFClCO_2H$ |
| $CCl_2=CFOR$ | $CHCl_2CO_2H$ |
| $CF_3CF=CFOR$ | $CF_3CHFCO_2H$ |
| $(CF_3)_2C=CFOR$ | $(CF_3)_2CHCO_2H$ |

Many carboxylic acids are generally stable under neutral or acidic conditions, but may be decarboxylated under basic conditions to produce a hydrofluorocarbon:

$$R_f^1R_f^2CHCO_2H \rightarrow R_f^1R_f^2CH_2+CO_2$$

Methods of decarboxylating secondary carboxylic acids are known in the chemical art. As an example of a suitable method, the addition of a stoichiometric amount of base (e.g., triethylamine) can be sufficient to cause decarboxylation and the production of a hydrofluorocarbon. Decarboxylation of fluoroalkyl carboxylates is described, for example, in *Chemistry of Organic Fluorine Compounds,* M. Hudlicky, pp. 496–500 (2nd ed. 1992).

As an alternative to decarboxylation, an alpha-hydrocarbonyl compound may be fluorinated to produce a more highly fluorinated or perfluorinated carbonyl compound. See, e.g., U.S. Pat. No. 5,573,654 (Cheburkov et al.) the description of which is incorporated herein by reference.

One specific embodiment of the process of the invention is the reaction of heptafluoroisobutenyl methyl ether with perfluorobutyl alkoxide to produce perfluorobutyl methyl ether and the conjugate base of alpha-hydro hexafluoroisobutanoyl fluoride; subsequently the conjugate base of alpha-hydro hexafluoroisobutanoyl fluoride can be hydrolyzed and then decarboxylated to form hexafluoropropane (HFC-236fa). The process can go specifically as follows:

First, heptafluoroisobutenyl methyl ether can be reacted with perfluorobutyl alkoxide according to the invention to produce perfluorobutyl methyl ether and the conjugate base of alpha-hydro hexafluoroisobutanoyl fluoride:

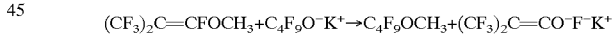

The perfluorobutyl alkoxide can be prepared in situ by contacting perfluorobutanoyl fluoride with anhydrous potassium fluoride as previously described. The perfluorobutyl methyl ether product can be easily separated from the non-volatile conjugate base, $(CF_3)_2C=CO^-FK^+$. The conjugate base may then be hydrolyzed to its carboxylic acid, which can be decarboxylated with aqueous base to form hexafluoropropane:

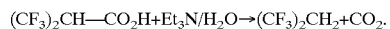

In the above preferred reaction scheme, the heptafluoroisobutenyl methyl ether reactant can be obtained from a number of commercial sources, or can be prepared from perfluoroisobutene (PFIB). One method involves the addition of methanol to perfluoroisobutene to produce octafluoroisobutyl methyl ether, followed by dehydrofluorination of the octafluoroisobutyl methyl ether to produce heptafluoroisobutenyl methyl ether, as shown:

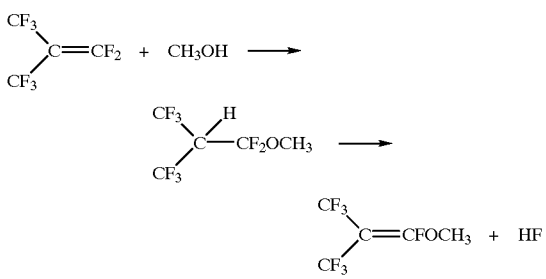

The alkoxylation (e.g., methoxylation, ethoxylation, etc., as desired) of perfluoroisobutene can be accomplished by methods known in the chemical art. One such method generally involves passing a gaseous stream containing perfluoroisobutene through methanol to produce octafluoroisobutyl methyl ether. The octafluoroisobutyl methyl ether can be dehydrofluorinated by any of a number of known methods, for example by refluxing the octafluoroisobutyl methyl ether in 15% aqueous potassium hydroxide at 100° C. to produce heptafluoroisobutenyl methyl ether. An example of a procedure for producing heptafluoroisobutenyl methyl ether is described in Koshar R. H., Simmons T. C., Hoffman F. W., J Am. Chem Soc. 79 1741 (1957), incorporated herein by reference.

Thus, an embodiment of the invention includes the steps of providing perfluoroisobutene; reacting the perfluoroisobutene with methanol to produce octafluoroisobutyl methyl ether; dehydrofluorinating the octafluoroisobutyl methyl ether to produce heptafluoroisobutenyl methyl ether; reacting the heptafluoroisobutenyl methyl ether with a fluorinated alkoxide (e.g., perfluorobutyl alkoxide) to produce a hydrofluoroether and a conjugate base of the fluorinated carbonyl compound; hydrolyzing the conjugate base of the fluorinated carbonyl compound to produce an alpha-hydro fluoroalkyl carboxylic acid; and decarboxylating the alpha-hydro fluoroalkyl carboxylic acid.

EXAMPLES

1. Reaction of potassium pentafluoropropoxide with 1-methoxyheptafluoro-1-isobutene (methylheptafluoroisobutenyl ether).

In a pressure glass reactor with magnetic bar stirrer, pentafluoropropionic acid fluoride (3.28 g, 75% purity 15 mmol) and potassium fluoride (1.27 g, 22 mmol) were heated in diglyme (8.7 g) for 30 min at 50° C., then held at 0° C. for 1 hour then cooled to −50° C. Methoxyfluoroisobutene (7.51 g, 96% purity, 34 mmol) was added to the solution and the mixture agitated at room temperature for 17 hours.

After warming to 45° C., the reactor was vented into a trap (−78° C.) and was collected 0.23 g of a mixture consisting of (GC %): 25% starting propionyl fluoride, 45.5% $C_3F_7OCH_3$, and 28% hexafluoropivaloyl fluoride $CH_3C(CF_3)_2C(O)F$ (an isomerization product of the methoxyfluoroisobutene). The remaining contents of the reactor were distilled into a trap (−78C.) under vacuum (25 torr at 40° C.) to yield 6.39 g of a liquid consisting of (GC %): 36.5% $C_3F_7OCH_3$, 55% the hexafluoropivaloyl fluoride and 3.5% the starting vinyl ether.

To the diglyme residue in the reactor was added 10 ml $H_2O$ (the solution had pH=4) and triethylamine (2.4 g) to raise the pH to 8. Distillation yielded a fraction with b.p. up to 100° C., 1.59 g, which is mainly triethylamine with purity 85% contaminated 10% diglyme (triethylamine recovery 56%), and 3.25 g of material which was recondensed in a second trap to give a 2.73g mixture (GC %): 87% $CF_3CH_2CF_3$, 8% $CF_3CH=CF_2$ (from dehydrofluorination), 2% $C_3F_7OCH_3$ and 1.5% $CH_3C(CF_3)_2C(O)F$ (C5 acid fluoride).

The product yields were calculated based on weights of all obtained liquid and gaseous products mixtures, and purity of starting materials. Yield of $C_3F_7OCH_3$, 86% on consumed pentafluoropropionic acid fluoride. Yield of $CF_3CH_2CF_3$, 50.1% and the hexafluoropivaloyl fluoride 49.5%.

2. Reaction of isomeric potassium perfluorobutoxides with 1-methoxyheptafluoro-1-isobutene (methylheptafluoroisobutenyl ether).

Using essentially the same procedure as in Example 1, an isomeric mixture of the perfluorobutyric acid fluorides (2.67 g with summary acyl fluorides content 81%, 10 mmol), potassium fluoride (0.78 g, 13 mmol), the 1-methoxyheptafluoro-1-isobutene (5.10 g, 96% purity, 23 mmol) was combined in 8.54 g diglyme and agitated at room temperature for 34 hours. The reactor was vented and 5.44 g of material collected in the trap. The material consisted of (GC %): 4.0% starting C4 acyl fluoride, 35.3% $C_4F_9OCH_3$, 58.5% hexafluoropivaloyl fluoride (C5 acid fluoride) and a trace (0.4%) of diglyme. To the diglyme residue was added 8.64 g $H_2O$ and 1.76 g triethylamine to yield 1.38 g $CF_3CH_2CF_3$ (after recondensation), and 95.5 % purity. The products yields were calculated based on the weight of obtained mixtures, their GC % content and purity of starting compounds. Yield of $C_4F_9OCH_3$ is 77% (from perfluorobutyric acid fluorides and 85% on the consumed fluorides). Yield of $CF_3CH_2CF_3$ is 39% and C5 acid fluoride −65%.

3. Reaction of potassium pentafluoropropoxide with 1-ethoxyheptafluoro-1-isobutene (ethylheptafluoroisobutenyl ether).

Using essentially the same procedure as in Example 1, pentafluoropropionyl fluoride (2.47 g, 11 mmol), KF (0.94 g, 16 mmol) and 1-ethoxyheptafluoro-1-isobutene (4.26 g, 16.5 mmol) in 7.44 g diglyme were agitated at room temperature for about 60 hours to yield 3.0 g of liquid consisting of (GC %): 80% $C_3F_7OC_2H_5$ and 5.5% starting vinyl ether. To the remaining diglyme solution was added equal volume of water and 1.8 g triethylamine (to pH 9) to yield 1.5 g of gas collected in the trap which comprised: 98 GC % $CF_3CH_2CF_3$ (including 10% of olefin $CF_3CH=CF_2$) plus 1% $C_3F_7OC_2H_5$. Triethylamine recovery (KOH addition to the solution and distillation) gave 2.62 g liquid material, which consisted of: 2% $CF_3CH_2CF_3$, 58% triethylamine, 8% the unreacted starting ethoxyfluoroisobutene and 21% diglyme. Calculated yields by GC: $C_3F_7OC_2H_5$ 105% based on acid fluoride used; $CF_3CH_2CF_3$, 67% based on the consumed vinyl ether.

4. Reaction of isomeric perfluorobutoxide mixture with 1-ethoxyheptafluoro-1-isobutene (ethylheptafluoroisobutenyl ether).

Using essentially the procedure as in Example 1, a mixture of perfluorobutyric acid fluorides (3.77 g with acyl fluoride content of 81%, 14 mmol), KF (1.02 g ,17 mmol), the ethoxyisobutene (4.56 g with purity 88%, 0.18 mmol) in 8.33 g diglyme was agitated at room temperature for four days. The reactor was vented to yield 0.67 g liquid which comprised (GC %): 88% starting acyl fluorides mixture and 8% $C_4F_9OC_2H_5$. The reaction solution remaining in the reactor was vacuum distilled to yield 3.0 g of a mixture which comprised (GC %): 75% $C_4F_9OC_2H_5$, 1.5% $C_2H_5C(CF_3)_2C(O)F$ and 7.6% starting vinyl ether. After decarboxylation by treatment with triethylamine, the remaining diglyme solution yielded 1.45 g $CF_3CH_2CF_3$ (purity 98% contaminated with 1.5% $C_4F_9OC_2H_5$ and 0.5% $(CF_3)CC_2H_5C(O)F)$. Triethylamine recovery gave 2.5 g organic liquid material with b.p. up to 101° C., consisting of (GC %): 2.5% $CF_3CH_2CF_3$, 42% triethylamine, 9% starting vinyl ether and 29% diglyme. Calculated yields were: $C_4F_9OC_2H_5$, 72% on the consumed acid fluoride mixture, $CF_3CH_2CF_3$, 75% on consumed vinyl ether.

5. Reaction of 1-trifluoromethyl-perfluoro-3-pentanone with 1-methoxy-1-perfluoroisobutyl ether.

Into a 500 ml three necked round bottomed flask equipped mechanical stirrer, Friedrichs condenser, calcium sulfate drying tube and a thermometer was placed anhydrous potassium fluoride (8.0 g, 0.138 moles), anhydrous diglyme(120 g), Adogen™ 464 (0.3 g), 1-trifluoromethyl-perfluoro-3-pentanone (99.2% assay, 32.4 g, 0.102 moles), and 1-methoxy-heptafluoroisobutylene (92% assay, 25.4 g, 0.11 moles). The light yellow heterogeneous mixture was stirred at ambient temperature overnight after which time solids had formed on the sides of the reaction flask. Heating to about 55° C. was applied for two hours followed by the gradual addition of water (50 ml) and triethylamine (12.0 gms, 0.119 moles). Some outgassing occurred during the water addition and liquid products were noted and collected in a −78° C. cold trap which was attached after the condenser.

The mixture was heated to reflux temperature to collect the liquid hydrofluoroether in a Barrett trap and low boiling products in the dry ice trap. A total of 22.6 gms of product was collected in the Barrett trap which GC revealed as $C_2F_5CF(OCH_3)CF(CF_3)_2$, 79%. The molar yield of $C_2F_5CF(OCH_3)CF(CF_3)_2$ was calculated to be 50%. The condensate in the −78° cold trap, 19.0 gms, contained some additional $C_2F_5CF(OCH_3)CF(CF_3)_2$ (~6.%), $CF_3CH_2CF_3$ (44%) along with some starting vinyl ether. The presence of the some unreacted starting ketone was detected by gc/ms analysis. A 46% molar yield $CF_3CH_2CF_3$ was realized.

What is claimed is:

1. A process to produce a hydrofluoroether by reacting a fluorinated alkoxide with an alkyl fluorovinylalkyl ether having alpha-beta carbon-carbon unsaturation relative to the ether oxygen, to produce a hydrofluoroether, wherein said alkyl fluorovinylalkyl ether is of the formula:

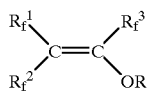

wherein $R_f^1$, $R_f^2$, and $R_f^3$ are each independently fluorine or a perfluorinated aliphatic having from 1 to 10 carbon atoms, and R is a linear or branched alkyl having from 1 to 6 carbon atoms.

2. The process of claim 1, wherein the alkyl fluorovinylalkyl ether is chosen from the group consisting of:

$CF_2$=$CFOR$,
$CF_3CF$=$CFOR$,
$(CF_3)_2C$=$CFOR$,
$(CF_3)_2C$=$C(C_2F_5)OR$,
$(CF_3)_2C(OR)C[CF(CF_3)_2]$=$C(OR)CF_3$,
$CF_3C(OR)$=$C[CF(CF_3)_2]_2$,
$CF_2$=$C(CF_3)C(CF_3)$=$CFOR$,
$C_2F_5CF(CF_3)C(C_2F_5)$=$CFOR$,
$C_2F_5CF(CF_3)C(CF_3)$=$C(CF_3)OR$, $CF_3(OR)$=$C(CF_3)C(CF_3)$=$C(OR)CF_3$,

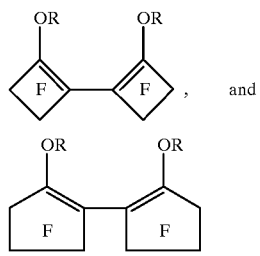

wherein each R independently comprises an alkyl.

3. The process of claim 1, wherein the fluorinated alkoxide has the general formula:

$R_f$—O−[Rf—O−]

wherein $R_f$ is a fluoroalkyl.

4. The process of claim 3, wherein $R_f$ contains from 1 to 10 carbon atoms.

5. The process of claim 3, wherein the fluorinated alkoxide is chosen from the group consisting of
$CF_3O^-M^+$,
$C_2F_5O^-M^+$,
$C_3F_7O^-M^+$,
$C_4F_9O^-M^+$,
$C_5F_{11}O^-M^+$,
$C_6F_{13}O^-M^+$,
$CF_3(O)C_2F_4O^-M^+$,
$(CF_3)_2CFO^-M^+$,
$(CF_3)_2NCF_2CF_2O^-M^+$,
$M^{+-}OC_3F_6O^-M^+$,

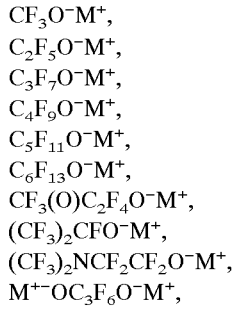

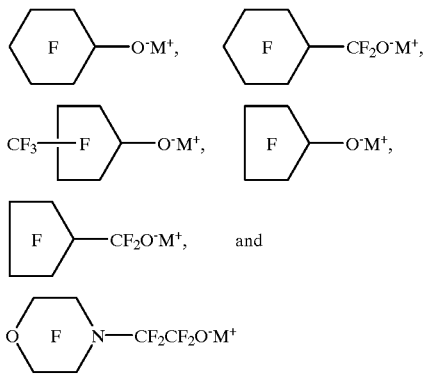

wherein $M^+$ is a cation.

6. The process of claim 1, wherein the hydrofluoroether has the general formula $R_f$—O—R, wherein $R_f$ is a fluoroalkyl having from 1 to 10 carbons, and R is an alkyl having from 1 to 6 carbons.

7. The process of claim 1, wherein the hydrofluoroether is chosen from the group consisting of $C_3F_7OCH_3$, $C_3F_7OC_2H_5$, $C_3F_7OC_3H_7$, $C_3F_7OC_4H_9$, $C_3F_7OC_5H_{11}$, $C_3F_7OC_6H_{13}$, $C_4F_9OCH_3$, $C_4F_9OC_2H_5$, $C_4F_9OC_3H_7$, $C_4F_9OC_4H_9$, $C_4F_9OC_5H_{11}$, $C_4F_9OC_6H_{13}$, $C_5F_{11}OCH_3$, $C_5F_{11}OC_2H_5$, $C_5F_{11}OC_3H_7$, $C_5F_{11}OC_4H_9$, $C_5F_{11}OC_5H_{11}$, $C_5F_{11}OC_6H_{13}$, $C_6F_{13}OCH_3$, $C_6F_{13}OC_2H_5$, $C_6F_{13}OC_3H_7$, $C_6F_{13}OC_4H_9$, $C_6F_{13}OC_5H_{11}$, $C_6F_{13}OC_6H_{13}$, $C_7F_{15}OCH_3$, $C_7F_{15}OC_2H_5$, $C_7F_{15}OC_3H_7$, $C_7F_{15}OC_4H_9$, $C_7F_{15}OC_5H_{11}$, $C_7F_{15}OC_6H_{13}$, $C_8F_{17}OCH_3$, $C_8F_{17}OC_2H_5$, $C_8F_{17}OC_3H_7$, $C_8F_{17}OC_4H_9$, $C_8F_{17}OC_5H_{11}$, $C_8F_{17}OC_6H_{13}$, $CF_3OC_3F_6OCH_3$, $C_2F_5OC_2F_4OC_2H_5$, $CH_3OC_4F_8OCH_3$

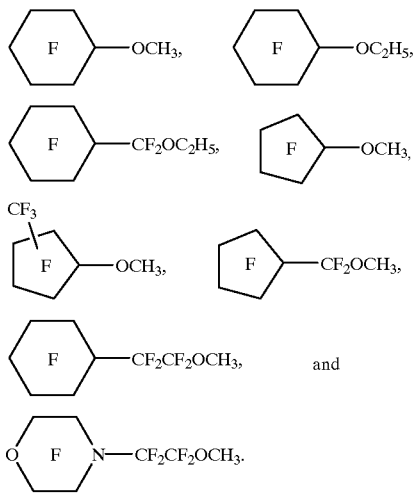

8. The process of claim 1, wherein a reaction product further comprises a conjugate base of a fluorinated carbonyl compound.

9. The process of claim 8, wherein the conjugate base of a fluorinated carbonyl compound has the mesomeric carbanion structure:

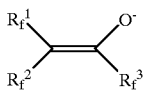

wherein $R_f^1$, $R_f^2$, and $R_f^3$ are independently fluorine atoms or fluorinated aliphatic groups.

10. The reaction of claim 8, wherein a conjugate acid of the fluorinated carbonyl compound is a compound chosen from the group consisting of:

$CHF_2COF$,
$CHFClCOF$,
$CHCl_2COF$,
$CF_3CHFCOF$,
$(CF_3)_2CHCOF$,
$(CF_3)_2CHC(O)C_2F_5$,
$(CF_3)_2C(OR)CH[(CF(CF_3)_2]C(O)CF_3$,
$CF_3C(O)CH[CF(CF_3)_2]_2$,
$CF_2=C(CF_3)CH(CF_3)COF$,
$C_2F_5CF(CF_3)CH(C_2F_5)COF$,
$C_2F_5CF(CF_3)CH(CF_3)COCF_3$,
$CF_3COCH(CF_3)CH(CF_3)COCF_3$,

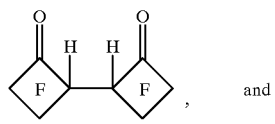 and

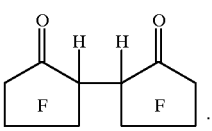.

11. The process of claim 1, wherein the fluorinated alkoxide is prepared from a fluorinated alkoxide precursor chosen from the group consisting of: a fluorinated acyl fluoride, a fluorinated acyl chloride, a fluoroalkyl ester, a fluoroalkyl carbonate, a fluorinated ketone, a fluorinated tertiary alcohol, and a fluoroalkyl anhydride.

12. The process of claim 11, wherein the fluorinated alkoxide is prepared by treating one and more fluorinated alkoxide precursors chosen from a fluorinated acyl fluoride, a fluorinated acyl chloride, a fluoroalkyl ester, a fluoroalkyl carbonate, or a fluoroalkyl anhydride with an anhydrous alkali metal fluoride in an anhydrous, polar, aprotic solvent to generate a fluorinated alkoxide.

13. The process of claim 12, wherein the fluorinated alkoxide precursor is chosen from the group consisting of $CF_3C(O)F$, $C_2F_5C(O)F$, $C_3F_7C(O)F$, $C_4F_9C(O)F$, $C_5F_{11}C(O)F$, $CF_3C(O)Cl$, $C_2F_5C(O)Cl$, $C_3F_7C(O)Cl$, $C_4F_9C(O)Cl$, $C_5F_{11}C(O)Cl$, $CF_3CO_2CF_3$, $C_2F_5CO_2C_2F_5$, $C_3F_7CO_2C_3F_7$, $C_4F_9CO_2C_4F_9$, $C_5F_{11}CO_2C_5F_{11}$, $CF_3C(O)-O-C(O)CF_3$, $C_2F_5C(O)-O-C(O)C_2F_5$, $C_3F_7C(O)-O-C(O)C_3F_7$, $C_4F_9C(O)-O-C(O)C_4F_9$, $C_5F_{11}C(O)-O-C(O)C_5F_{11}$, $CF_3OC(O)OCF_3$, $CF_3CF_2OC(O)OCF_2CF_3$, $C_3F_7OC(O)OC_3F_7$,

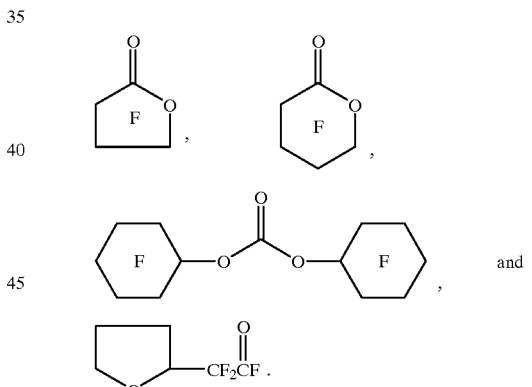

14. The process of claim 11, wherein the fluorinated alkoxide is prepared by treating a fluoroketone with an anhydrous alkali metal fluoride to generate a secondary fluoroalkoxide.

15. The process of claim 14, wherein the fluoroketone is chosen from the group consisting of $CF_3COCF_3$, $C_2F_5COC_2F_5$, $C_3F_7COC_3F_7$, $C_4F_9COC_4F_9$, $C_4F_9COCF_3$, $HC_4F_8COCF_3$,

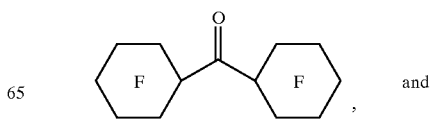,

-continued

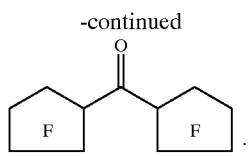

16. The process of claim 11, wherein the fluorinated alkoxide is prepared by treating a fluorinated tertiary alcohol with a base to produce a fluorinated tertiary alkoxide.

17. The process of claim 16, wherein the fluorinated tertiary alcohol is chosen from the group consisting of $(CF_3)_3COH$, $(CF_3)_2C(C_2F_5)OH$, and $(CF_3)_2CFCF_2C(CF_3)_2OH$.

18. A process for preparing a hydrofluoroether, the process comprising the steps of:
providing octafluoroisobutylene;
reacting the octafluoroisobutylene with methanol to produce octafluoroisobutyl methyl ether;
dehydrofluorinating the octafluoroisobutyl methyl ether to form heptafluoroisobutenyl methyl ether; and
reacting the heptafluoroisobutenyl methyl ether with a fluorinated alkoxide wherein the reaction product of heptafluoroisobutenyl methyl ether with a fluorinated alkoxide comprises a hydrofluoroether and a conjugate base of a fluorinated carbonyl compound.

19. The process of claim 18, further comprising a step of hydrolyzing the conjugate base of a fluorinated carbonyl compound.

20. The process of claim 19, further comprising a step of decarboxylating the hydrolyzed conjugate base of a fluorinated carbonyl compound to produce a hydrofluorocarbon.

21. The process of claim 20, wherein the hydrofluorocarbon comprises a hexafluoropropane.

22. A process for preparing a hydrofluoroether and a hydrofluorocarbon comprising the steps of
providing an alkyl fluorovinylalkyl ether;
providing a fluorinated alkoxide;
reacting the alkyl fluorovinylalkyl ether with the fluorinated alkoxide to produce a hydrofluoroether and a conjugate base of a fluorinated carbonyl compound;
contacting the conjugate base of a fluorinated carbonyl compound with water to produce an alpha-hydro carboxylic acid; and
decarboxylating the alpha-hydro carboxylic acid to form a hydrofluorocarbon.

23. The process of claim 22, comprising the steps of:
providing heptafluoroisobutenyl methyl ether by reacting perfluoroisobutene with methanol to produce octafluoroisobutyl methyl ether, and dehydrofluorinating the octafluoroisobutyl methyl ether to produce heptafluoroisobutenyl methyl ether;
reacting the heptafluoroisobutenyl methyl ether with a fluorinated alkoxide to produce a hydrofluoroether and a conjugate base of a fluorinated carbonyl compound;
hydrolyzing the conjugate base of a fluorinated carbonyl compound to produce an alpha-hydro fluoroalkyl carboxylic acid; and
decarboxylating the alpha-hydro fluoroalkyl carboxylic acid to produce a hydrofluorocarbon.

24. The process of claim 23, wherein the hydrofluorocarbon comprises a hexafluoropropane.

* * * * *